United States Patent [19]

Bell

[11] Patent Number: 4,720,353

[45] Date of Patent: Jan. 19, 1988

[54] STABLE PHARMACEUTICAL W/O EMULSION COMPOSITION

[75] Inventor: Stephen R. Bell, Harwinton, Conn.

[73] Assignee: Richardson-Vicks Inc., Wilton, Conn.

[21] Appl. No.: 38,216

[22] Filed: Apr. 14, 1987

[51] Int. Cl.$^4$ .............................................. B01J 13/00
[52] U.S. Cl. .................................... 252/309; 514/859; 514/887; 514/937
[58] Field of Search ................ 252/309; 514/859, 887, 514/937

[56] References Cited

U.S. PATENT DOCUMENTS

| | | | |
|---|---|---|---|
| 4,466,955 | 8/1984 | Calvo et al. | 424/62 |
| 4,532,132 | 7/1985 | Keil | 514/937 X |
| 4,563,346 | 1/1986 | Deckner | 514/859 X |
| 4,613,592 | 9/1986 | Benzoni | 514/859 X |
| 4,665,116 | 5/1987 | Kornhaber et al. | 524/268 |
| 4,673,570 | 6/1987 | Soldati | 424/66 |
| 4,687,843 | 8/1987 | Smolin et al. | 514/873 X |

FOREIGN PATENT DOCUMENTS

3436177A1  4/1986  Fed. Rep. of Germany ...... 252/309

Primary Examiner—Matthew A. Thexton
Attorney, Agent, or Firm—Salvatore R. Conte

[57] ABSTRACT

A stable water-in-oil emulsion composition for topical therapeutic administration comprising:

a. a dispersed aqueous phase comprising water optionally containing a pharmaceutically acceptable electrolyte dissolved therein;
b. a pharmaceutically acceptable continuous oil phase comprising mineral oil and a volatile silicone fluid;
c. an organopolysiloxane emulsifier of Formula (I) hereinafter described;
d. PPG-20 Methyl Glucose Ether Distearate; and
e. an active drug component for topical application.

8 Claims, No Drawings

STABLE PHARMACEUTICAL W/O EMULSION COMPOSITION

The subject invention relates to the field of pharmaceutical emulsion compositions and, more particularly, to stable water-in-oil emulsion compositions for topical therapeutic administration comprising:

a. a dispersed aqueous phase comprising water optionally containing a pharmaceutically acceptable electrolyte dissolved therein;
b. a pharmaceutically acceptable continuous oil phase comprising mineral oil and a volatile silicone fluid;
c. an organopolysiloxane emulsifier of Formula (I) hereinafter described;
d. PPG-20 Methyl Glucose Ether Distearate; and
e. an active drug component for topical application.

The disclosure of German Patent Publication No. DE 3436177 A1 (April, 1986), incorporated herein by reference, is pertinent background for this invention because it relates to the use of said organopolysiloxane emulsifier for producing water-in-oil (w/o) emulsions whose oil phase consists of or contains silicone oil. As described therein, the oil phase of the w/o emulsion may contain mineral oil (among other carbon-organic oils or waxes) in addition to the silicone oil. An exemplified silicone oil is the low viscosity silicone fluid, octamethylcyclotetrasiloxane. Also exemplified is the use of an electrolyte (e.g. NaCl) in the aqueous discontinuous phase to provide heat stability against separation of the emulsion. The emulsifier component is an organopolysiloxane-polyoxyalkylene block copolymer with silicon atom-bound long chain alkyl groups, as more fully described hereinafter (Formula I).

The aforementioned silicone oil, octamethylcyclotetrasiloxane, belongs to a class of cyclic siloxanes which are volatile, low viscosity silicone fluids known by their chemical name as polydimethylcyclosiloxanes and by their CTFA (Cosmetic, Toiletry and Fragrance Association) name as cyclomethicones. Said cyclomethicones are useful ingredients in a wide range of cosmetic and personal care formulations. These volatile silicone fluids provide several beneficial properties to such formulations including, for example, lubricity, feel and detackification and, furthermore, they evaporate without leaving a residue.

It has been found, however, that when said volatile silicone fluids are incorporated into the aforementioned water-in-mineral oil emulsion compositions, the resultant emulsion is subject to instability and separation upon standing. This, despite the presence of the organopolysiloxane emulsifier and the electrolyte stabilizer.

It is an object of the present invention, therefore, to provide a stable pharmaceutical emulsion composition which comprises an effective therapeutic amount of a topical drug component, a water-containing phase (optionally containing a pharmaceutically acceptable electrolyte) dispersed in a mineral oil continuous oil phase containing a volatile silicone fluid and said organopolysiloxane emulsifier. It is a further object of this invention to provide such stable emulsion compositions by incorporating therein an effective stabilizing amount of a particular esterified propoxylated glucose derivative.

The foregoing objects are provided by the composition of this invention which, in more detail, comprises:
(a) a dispersed aqueous phase comprising water optionally containing a pharmaceutically acceptable electrolyte dissolved therein;
(b) a pharmaceutically acceptable continuous oil phase comprising mineral oil and a volatile silicone fluid;
(c) an organopolysiloxane of the average formula:

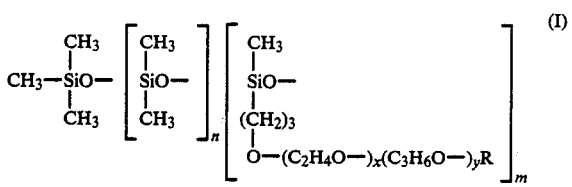

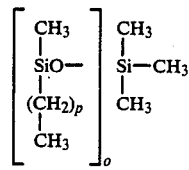

wherein
R is hydrogen or $C_{1-4}$ alkyl, preferably methyl;
n is a number between 10 and 200;
m is a number between 1 and 25;
o is a number between 1 and 100, provided that all $o > m$;
p is a number between 7 and 17;
and the molar weight of $(C_2H_4O-)_x(C_3H_6O-)_yR$ is between 250 and 2000, in which x and y are such that the weight ratio of oxyethylene ($C_2H_4O-$) groups to oxypropylene ($C_3H_6O-$) groups is between 100:0 to 20:80.
(d) PPG-20 Methyl Glucose Ether Distearate; and
(e) an effective therapeutic amount of a topically active drug component.

Preferred organopolysiloxanes of Formula I are those wherein R is hydrogen or methyl; n is about 25-150; m is about 1-15; and o is about 5-50 with $o > 2$ m; the molar weight of $(C_2H_4O-)_x(C_3H_6O-)_yR$ is about 400-1200; and the weight ratio of oxyethylene to oxypropylene groups is about 400-1200. Of said preferred organopolysiloxanes, a particularly preferred embodiment, wherein R is hydrogen and p is 15, has the CTFA name, Cetyl Dimethicone Copolyol, and is available under the product name ABIL B 9806 from its supplier, the Goldschmidt Chemical Corporation, Hopewell, Va.

The organopolysiloxanes of Formula (I) are identified in the aforementioned No. DE 3436177 A1 reference as having been previously reported. Furthermore, said reference discloses how to use same in making water-in-oil emulsion compositions containing silicone oil. As noted previously, however, the stability of such water-in-mineral oil emulsion compositions have been found to be detrimentally influenced when certain volatile silicone fluids are incorporated therein.

The term "volatile silicone fluid" herein refers to a polydimethylcyclosiloxane, also known as a cyclic dimethyl polysiloxane, a compound that conforms to the formula:

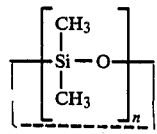

wherein n is an integer between 4 and 6. Accordingly, the term "volatile silicone fluid" herein refers to a member selected from the group consisting of octamethylcyclotetrasiloxane, decamethylcyclopentasiloxane, dodecamethylcyclohexasiloxane and mixtures thereof.

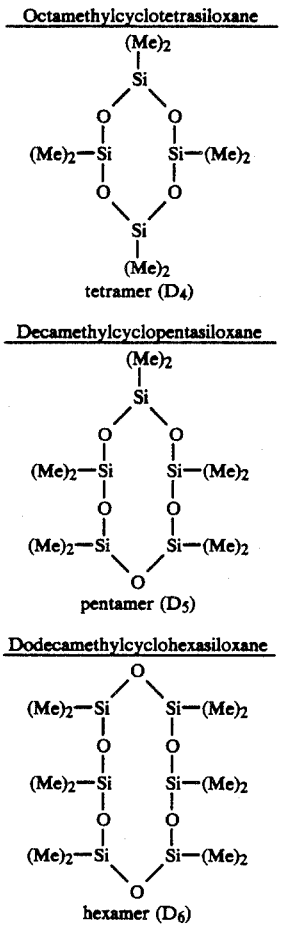

Said volatile silicone fluids, which have known applications as additives in topical cosmetic formulations, are readily available from diverse commercial distributors, for example, from Dow Corning Corporation, Midland, Mich., under its trademark names, for example:

| | |
|---|---|
| Dow Corning ® 244 Fluid | $D_4$ tetramer; |
| Dow Corning ® 245 Fluid | $D_4$ tetramer and $D_5$ pentamer mixture; |
| Dow Corning ® 344 Fluid | $D_5$ pentamer; and |
| Dow Corning ® 345 Fluid | $D_4$ tetramer, $D_5$ pentamer and $D_6$ hexamer mixture. |

Other sources identified in the CTFA Cosmetic Dictionary, 3rd Edition, include the SF-1173 and SF-1202 Silicone Fluids from General Electric Company, Silicone Products Division, Waterford, N.Y., and the relevant SWS-numbered products from Stauffer Chemical Company, SWS Silicones Division, Adrian, Mich.

It has been found that water-in-mineral oil emulsions which contain a volatile silicone fluid, are subject to instability, notwithstanding the presence of the organopolysiloxane emulsifier of Formula (I) and an electrolyte stabilizer. To overcome such disadvantage, a co-emulsifying surfactant is generally employed to enhance the stability of the emulsion. Typical of such co-emulsifying surfactants are Tergitol ® 1553 (polyethylene glycol ether of a mixture of $C_{11}$ to $C_{15}$ fatty alcohols with an average of 3 mols of ethylene oxide, from Union Carbide Corporation, Danbury, Conn.); polyalcohol fatty acid esters such as oleic acid ester or isostearic acid ester of glycerin, polyglycerin or sorbitol and wood wax alcohol, e.g., triglycerine trioleate; and the like;

As shown in Example 2 hereinafter, the same composition, absent said additional co-emulsifier, exhibits unacceptable signs of emulsion stability such as cracking, oil leeching or syneresis, and the like.

It has now been found that a particular esterified propoxylated glucose derivative, having the CTFA adopted name: PPG-20 Methyl Glucose Ether Distearate, provides a marked stabilizing effect on water-in-mineral oil emulsions containing a volatile silicone fluid in the mineral oil phase and organopolysiloxane emulsifier of Formula (I). Said glucose derivative effectively eliminates the need of an additional co-emulsifying surfactant, as noted above.

The stabilizing effect attributable to said esterified propoxylated glucose derivative is considered surprising and unexpected in light of the prior usage attributed thereto by its commercial supplier (Amerchol Corporation, Edison, N.J. under its trademark: GLUCAM ® P-20 Distearate) as a skin moisturizer and emollient, but not as an emulsifying surfactant, in oil-in-water type emulsions, which emulsions are opposite the subject water-in-oil type emulsions. That said esterified propoxylated glucose derivative provides such a stabilizing effect is deemed even more unobvious since, as shown in Example 3 hereinafter, the corresponding esterified ethoxylated glucose derivative fails to provide such stabilization. Furthermore, the stabilizing effect is achieved even without the necessity of an electrolyte salt in the aqueous phase.

Accordingly, the present invention provides a stable water-in-mineral oil emulsion carrier for various medicaments and drugs intended for topical skin application for example, water soluble, miscible or dispersible drugs may be incorporated into the aqueous phase of the w/o emulsion, and oil soluble, miscible or dispersible drugs may be incorporated into the oil phase of the w/o emulsion. A preferred embodiment of the present invention is one wherein said drug is an anti-acne active ingredient such as, for example, benzoyl peroxide, sulfur, resorcinol, salicylic acid, derivatives of retinoic acid, chlorhydroxyquinoline, and the like. Other examples of drugs suitable for topical application in the subject compositions include, without limitation thereto, non-steroidal antiinflammatory drugs such as ibuprofen, tolmetin and the like; and antibiotics such as erythromycin, tetracycline and the like. The amount of incorporated drug is an effective therapeutic amount for the particular drug indication. The subject compositions provide surprisingly effective skin penetration for the drug component.

In the emulsion compositions of the present invention, the aforementioned components are preferably employed in the following ranges, based on the weight of the composition:

| | % w/w |
|---|---|
| A. Oil Phase: | |

-continued

|  | % w/w |
|---|---|
| Mineral Oil | 1-15 |
| Organopolysiloxane Emulsifier | 1-4 |
| Volatile Silicone Fluid | 5-30 |
| PPG-20 Methyl Glucose Ether Distearate | 1-10 |
| B. Water Phase: | |
| Electrolyte Salt | 0-5 |
| Water, q.s. 100% | |
| C. Drug: a therapeutically effective amount in A or B or both but not exceeding 20% w/w of the total composition. | |

The viscosity of the mineral oil preferably has a value of less than 100 centitokes at 25° C. With regard to the organopolysiloxane emulsifier, from about 1.5 to about 3.0 weight percent is most preferred, and with regard to the PPG-20 methyl glucose ether distearate, from about 3 to about 8 weight percent is most preferred. Although the electrolyte salt is an optional additive, from about 0.1 to about 5 weight percent is preferred and from about 0.5 to about 2 weight percent is most preferred. Typical electrolytes include sodium chloride (preferred), sodium acetate, sodium citrate, magnesium stearate, sodium phosphate, calcium chloride, ammonium carbonate and the like.

The form of the compositions of this invention can range from freely flowing lotions to stiff creams, the exact form being largely determined by standard factors known to the skilled formulator such as the ratio of aqueous phase to oil phase, the mechanical mixing or shearing speed, and the like.

The emulsion compositions of this invention can be prepared in the conventional manner known to skilled formulators, typically by admixing the separately prepared aqueous phase with the separately prepared oil phase, using sufficient agitation and/or shear to uniformly disperse the aqueous phase as droplets generally having a size of less than 10 micrometers and preferably less than 1 micrometer, in the oil phase. Mild heating of the components can be used, if desired, to aid in the admixing, with, however, care being taken not to heat to a temperature which would vaporize the volatile silicone fluid component.

The subject compositions may also contain, as optional additions, one or more soluble or dispersible pharmaceutically acceptable ingredients generally used in pharmaceutical emulsion compositions for topical use. Typical such ingredients include, for example, a preservative or antioxidant such as methyl or propyl paraben, butylated hydroxyanisole, imidazolidinyl urea and the like; a water or oil soluble vitamin such as vitamin C, tocopheryl linoleate and the like; and/or a colorant, odorant, humectant, thickener and the like. In general, from about 0.1 to about 15 percent total weight of such optional additives may be incorporated into the subject compositions. Depending upon the solubility or miscibility characteristic of the particular additive, it can be incorporated into whichever emulsion phase is most suitable.

The compositions of the present invention are further illustrated, but not limited, by the following examples.

EXAMPLE 1

This example illustrates stable water-in-mineral oil compositions of the invention containing the antiacne drug components, benzoyl peroxide (in A), and both sulfur and resorcinol (in B), and the non-steroidal anti-inflammatory agent, ibuprofen (in C). Unless otherwise specified, the indicated ingredients are named by either their chemical or CTFA adopted name.

| Ingredients | % w/w | | |
|---|---|---|---|
| | A | B | C |
| A. Oil Phase: | | | |
| Cyclomethicone | 15.0 | 15.0 | 15.0 |
| Cyclomethicone & Quaterium-18 Hectorite & SD Alcohol 40[a] | 1.0 | 1.0 | 1.0 |
| Cetyl Dimethicone Copolyol | 2.0 | 2.0 | 2.0 |
| PPG-20 Methyl Glucose Ether Distearate | 5.0 | 5.0 | 5.0 |
| Benzoyl Peroxide | 10.0 | — | — |
| Sulfur | — | 8.0 | — |
| Ibuprofen | — | — | 2.0 |
| Mineral Oil | 2.0 | 2.0 | 2.0 |
| B. Water Phase: | | | |
| Sodium Chloride | 1.0 | 1.0 | — |
| Imidazolidinyl Urea | 0.1 | 0.1 | 0.1 |
| Resorcinol | — | 2.0 | — |
| Water, q.s. to 100% | | | |

[a] Bentone Gel VS-5, NL Chemicals, Hightstown, New Jersey.

In separate mixing vessels equipped with a mechanical stirrer, the water phase ingredients and the oil phase ingredients are added together and uniformly mixed. Note: in C, separately mix together and heat to about 50°-60° C. the Methyl Glucose Ether Distearate and ibuprofen until clear, then cool and add to other oil phase ingredients. The water phase is slowly added to the oil phase using high speed mechanical dispersing means and mixing is continued until a homogeneous w/o emulsion in liquid-cream form is obtained.

The emulsions of this example are stable and without signs of separation for over six months. When applied on to afflicted skin areas in the conventional manner, effective delivery of the drug component is provided.

EXAMPLE 2

A w/o emulsion from the indicated respective formulations are prepared.

| Ingredients | % w/w | | | |
|---|---|---|---|---|
| | A | B | C | D |
| A. Oil Phase | | | | |
| Cetyl Dimethicone Copolyol | 2.0 | 2.0 | 2.0 | 2.0 |
| Mineral Oil | 7.5 | 7.5 | 7.5 | 7.5 |
| Cyclomethicone | 22.0 | 22.0 | 22.0 | 22.0 |
| PPG-20 Methyl Glucose Ether Distearate | 0 | 1.0 | 5.0 | 10.0 |
| B. Water Phase: | | | | |
| Sodium Chloride | 1.0 | 1.0 | 1.0 | 1.0 |
| Water, q.s. to 100% | | | | |

The separately prepared oil and water phases are mixed together in the conventional manner to form a homogeneous emulsion for each of A, B, C and D. Each emulsion is characterized as a readily fluid liquid with an average viscosity of less than 1500 cps. As shown below, the A emulsion, without the esterified propoxylated glucose derivative, separates within 12 hours whereas emulsions B, C and D remain stable even after the 2 week test period.

| Time | A | B | C | D |
|---|---|---|---|---|
| 12 hours | x | s | s | s |
| 24 hours | x | s | s | s |
| 1 week | x | s | s | s |

| Time | A | B | C | D |
|---|---|---|---|---|
| 2 weeks | x | s | s | s | x = unstable;
s = stable

EXAMPLE 3

In this example, an esterified ethoxylated glucose derivative, PEG-20 Methyl Glucose Ether Distearate, is substituted for the esterified propoxylated glucose derivative of this invention.

| Ingredients | % w/w |
|---|---|
| A. Oil Phase: | |
| Cetyl Dimethicone Copolyol | 2.0 |
| Mineral Oil | 8.0 |
| Cyclomethicone | 10.0 |
| PEG-20 Methyl Glucose Ether Distearate | 10.0 |
| B. Water Phase: | |
| Sodium Chloride | 2.0 |
| Water, q.s. to 100% | |

The oil phase ingredients are separately mixed together using a high speed mixer until the PEG-20 Methyl Glucose Ether Distearate is dissolved and a homogeneous mixture is obtained. The sodium chloride is dissolved in the water and the saline water phase is slowly added to the oil phase with continued mixing for 5 minutes. Addition of the water phase results in separation of the PEG-20 Methyl Glucose Ether Distearate out of solution and no formation of an emulsion.

I claim:

1. A stable water-in-oil emulsion composition comprising:
   a. a dispersed water phase comprising water optionally containing a pharmaceutically acceptable electrolyte dissolved therein;
   b. a pharmaceutically acceptable continuous oil phase comprising mineral oil and a volatile silicone fluid selected from the group consisting of octamethylcyclotetrasiloxane, decamethylcyclopentasiloxane, dodecamethylcyclohexasiloxane and mixtures thereof dissolved therein;
   c. an organopolysiloxane of the average formula:

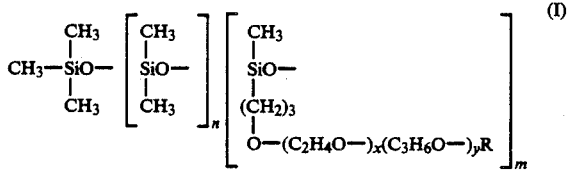

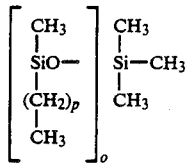

(I)

wherein
R is hydrogen or $C_{1-4}$ alkyl;
n is a number between 10 and 200;
m is a number between 1 and 25;
o is a number between 1 and 100, provided that all o>m;
p is a number between 7 and 17;
and the molar weight of $(C_2H_4O-)_x(C_3H_6O-)_yR$ is between 250 and 2000, in which x and y are such that the weight ratio of oxyethylene $(C_2H_4O-)$ groups to oxypropylene $(C_3H_6O-)$ groups is between 100:0 to 20:80.
   d. PPG-20 Methyl Glucose Ether Distearate; and
   e. an effective therapeutic amount of a topically active drug.

2. The composition of claim 1 falling within the following ranges:

| | % w/w |
|---|---|
| A. Oil Phase: | |
| Mineral Oil | 1–15 |
| Organopolysiloxane | 1–4 |
| Volatile Silicone Fluid | 5–30 |
| PPG-20 Methyl Glucose Ether Distearate | 1–10 |
| B. Water Phase: | |
| Electrolyte | 0–5 |
| Water, q.s. 100% | | and a therapeutically effective amount of said drug in A or B or both but not exceeding 20% w/w of the total composition.

3. The composition of claim 2 where in said organopolysiloxane: R is hydrogen or methyl; n is about 25–150; m is about 1–15 ; and o is about 5–50 with o>2 m; the molar weight of $(C_2H_4O-)_x(C_3H_6O-)_yR$ is about 400–1200; and the weight ratio of oxyethylene to oxypropylene groups is about 400–1200.

4. The composition of claim 2 wherein the amount of said organopolysiloxane is from about 1.5 to about 3.0 weight percent.

5. The composition of claim 2 wherein the amount of said PPG-20 Methyl Glucose Ether Distearate is from about 3 to about 8 weight percent.

6. The composition of claim 2 wherein said drug is an anti-acne agent.

7. The composition of claim 6 wherein said anti-acne agent is selected from the group consisting of benzoyl peroxide, sulfur, and resorcinol.

8. The composition of claim 2 wherein said drug is ibuprofen.

* * * * *